United States Patent
Mehr

(10) Patent No.: US 9,579,504 B2
(45) Date of Patent: Feb. 28, 2017

(54) PERSONALIZED PATIENT CONTROLLED NEUROSTIMULATION SYSTEM

(75) Inventor: Saeed Mehr, San Francisco, CA (US)

(73) Assignee: Robert Bosch LLC, Palo Alto, CA (US)

( * ) Notice: Subject to any disclaimer, the term of this patent is extended or adjusted under 35 U.S.C. 154(b) by 1595 days.

(21) Appl. No.: 12/822,374

(22) Filed: Jun. 24, 2010

(65) Prior Publication Data

US 2011/0319961 A1    Dec. 29, 2011

(51) Int. Cl.
  *A61N 1/36*     (2006.01)
  *A61N 1/372*    (2006.01)

(52) U.S. Cl.
  CPC ..... *A61N 1/36007* (2013.01); *A61N 1/36053* (2013.01); *A61N 1/37282* (2013.01); *A61N 1/36085* (2013.01)

(58) Field of Classification Search
  USPC ....................................... 607/40, 45
  See application file for complete search history.

(56) References Cited

U.S. PATENT DOCUMENTS

| | | | |
|---|---|---|---|
| 6,879,859 B1 | 4/2005 | Boveja | 607/45 |
| 2004/0059393 A1* | 3/2004 | Policker et al. | 607/40 |
| 2005/0004621 A1 | 1/2005 | Boveja et al. | 607/45 |
| 2005/0049655 A1 | 3/2005 | Boveja et al. | 607/58 |
| 2006/0247719 A1 | 11/2006 | Maschino et al. | 607/40 |
| 2006/0265022 A1* | 11/2006 | John et al. | 607/45 |
| 2007/0255334 A1* | 11/2007 | Keimel et al. | 607/40 |
| 2008/0009913 A1* | 1/2008 | Errico et al. | 607/40 |

FOREIGN PATENT DOCUMENTS

| | | |
|---|---|---|
| WO | WO 02/062291 A2 | 8/2002 |
| WO | WO 2006/010025 A2 | 1/2006 |
| WO | WO 2006/012423 A1 | 2/2006 |
| WO | WO 2006/055849 A1 | 5/2006 |
| WO | WO 2006/073915 A2 | 7/2006 |

\* cited by examiner

*Primary Examiner* — Allen Porter, Jr.
(74) *Attorney, Agent, or Firm* — Maginot, Moore & Beck LLP

(57) ABSTRACT

A method for personalized patient controlled neurostimulation is disclosed. The method generally includes steps (A) to (D). Step (A) may obtain (i) physical data of an individual and (ii) one or more manual inputs from the individual. Step (B) may generate compare data in a processor circuit by comparing the physical data with profile data of the individual. Step (C) may generate customized data by processing the one or more manual inputs and the compared data using a set of rules. The rules are generally (i) reprogrammable and (ii) govern generation of a nerve stimulation signal having predetermined control characteristics applicable to the individual. Step (D) may control the neurostimulation of the individual with the nerve stimulation signal based on the customized data.

7 Claims, 9 Drawing Sheets

PERSONALIZED PATIENT CONTROLLED NEUROSTIMULATION SYSTEM

FIELD OF THE INVENTION

The present invention relates to behavior management generally and, more particularly, to a method and/or apparatus for implementing a personalized patient controlled neurostimulation management system.

BACKGROUND OF THE INVENTION

Obesity has been shown be treatable by stimulation of a vagus nerve through an implantable device to create a feeling of satiety. Attempts have been made to automate the vagus nerve stimulation based on monitoring of swallows, rhythms or other data in a closed system. Vagus nerve stimulation amplitudes are commonly based on the amplitude of electrical signals in the nerve being stimulated. However, no evidence exists that the stimulation amplitude should be matched to the nerve signal amplitude. In addition, every patient is different and so individualized treatment for a given patient is more likely to be successful. Moreover, patient behavior should be managed for the treatment to be successful.

SUMMARY OF THE INVENTION

The present invention concerns a method for personalized patient controlled neurostimulation. The method generally includes steps (A) to (D). Step (A) may obtain (i) physical data of an individual and (ii) one or more manual inputs from the individual. Step (B) may generate compare data in a processor circuit by comparing the physical data with profile data of the individual. Step (C) may generate customized data by processing the one or more manual inputs and the compared data using a set of rules. The rules are generally (i) reprogrammable and (ii) govern generation of a nerve stimulation signal having predetermined control characteristics applicable to the individual. Step (D) may control the neurostimulation of the individual with the nerve stimulation signal based on the customized data.

The objects, features and advantages of the present invention include providing a method and/or apparatus for implementing a personalized patient controlled neurostimulation system that may (i) eliminate inadvertent stimulation, (ii) provide personalized neurostimulation, (iii) increase effectiveness of therapy by dynamic calibration of a neurostimulation signal and/or (iv) dynamically adapt the neurostimulation to a profile of the patient.

BRIEF DESCRIPTION OF THE DRAWINGS

These and other objects, features and advantages of the present invention will be apparent from the following detailed description and the appended claims and drawings in which:

DETAILED DESCRIPTION OF THE PREFERRED EMBODIMENTS

Embodiments of the present invention generally relate to obesity management systems having an implantable controller circuit, sensor array circuit, an interactive patient communication unit and a remote server computer. The timing, amplitude and frequency of neurostimulation signals generated by the implantable controller may be controlled directly by a patient (or individual) to personalize therapy for the patient to maximize the benefit. The sensor array may be used to supply patient data to an interactive coaching program in the remote server computer via the interactive patient communication unit. The coaching program may create information sent to and presented by the interactive patient communication unit to the patient. The information generally aids the patient in learning to calibrate optimally and control the neurostimulation.

The implantable controller may be configured by an internal calibration unit. The configurations are generally based on a rules program (e.g., script) that uses the sensor array data with user inputs from the patient to determine the timing, the frequency, the pulse width and the amplitude of the neurostimulation signals. A rule engine within the calibration unit may compensate for any signal degradation received from the sensor array to ensure optimal neurostimulation signals on a case by case basis. Diagnostic and therapeutic data is generally collected by the implantable controller and transmitted to a remote server computer. Healthcare professionals may monitor the resulting diagnostic and therapeutic data to assist the patient in optimizing the therapy. The above techniques and equipment may also be used for other neurostimulation and coaching programs related to other subjectively diagnosed and treated disorders including, but not limited to, addictive disorders, mental health conditions, obesity and pain.

Figure 1:
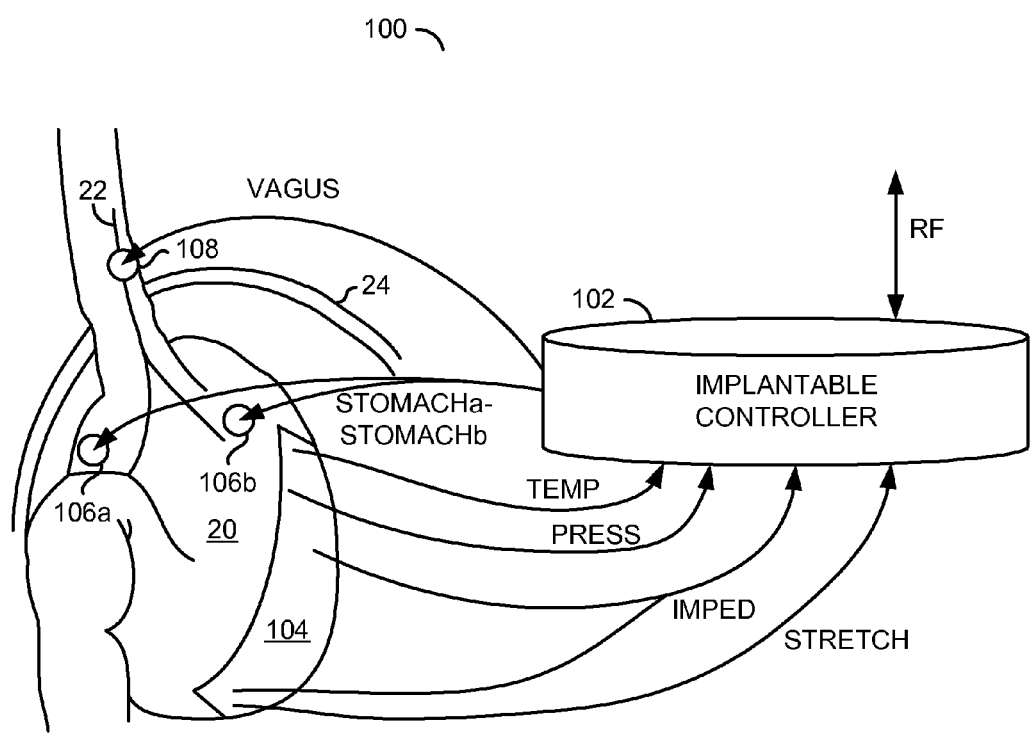
FIG. 1 is a diagram of example arrangement of a portion of a system proximate a stomach of a patient.

Referring to FIG. 1, a diagram of example arrangement of a portion of a system 100 proximate a stomach 20 of a patient is shown. The system (or apparatus) 100 generally comprises a circuit (or unit) 102, a circuit (or unit) 104, one or more circuits (or units) 106a-106b and a circuit (or unit) 108. A signal (e.g., VAGUS) may be generated by the circuit 102 and presented to the circuit 108. One or more signals (e.g., STOMACHa-STOMACHb) may be generated by the circuit 102 and presented to the circuits 106a-106b. The circuit 104 may generate a signal (e.g., TEMP) which is presented to the circuit 102. A signal (e.g., PRESS) may also be generated by the circuit 104 and presented to the circuit 102. A signal (e.g., IMPEL) may be generated by the circuit 104 and presented to the circuit 102. The circuit 104 may also generate a signal (e.g., STRETCH) that is presented to the circuit 102. A signal (e.g., RF) may be bidirectionally exchanged between the circuit 102 and an external device. The circuits 102-108 may be implemented in hardware, firmware and/or software.

Figure 2:
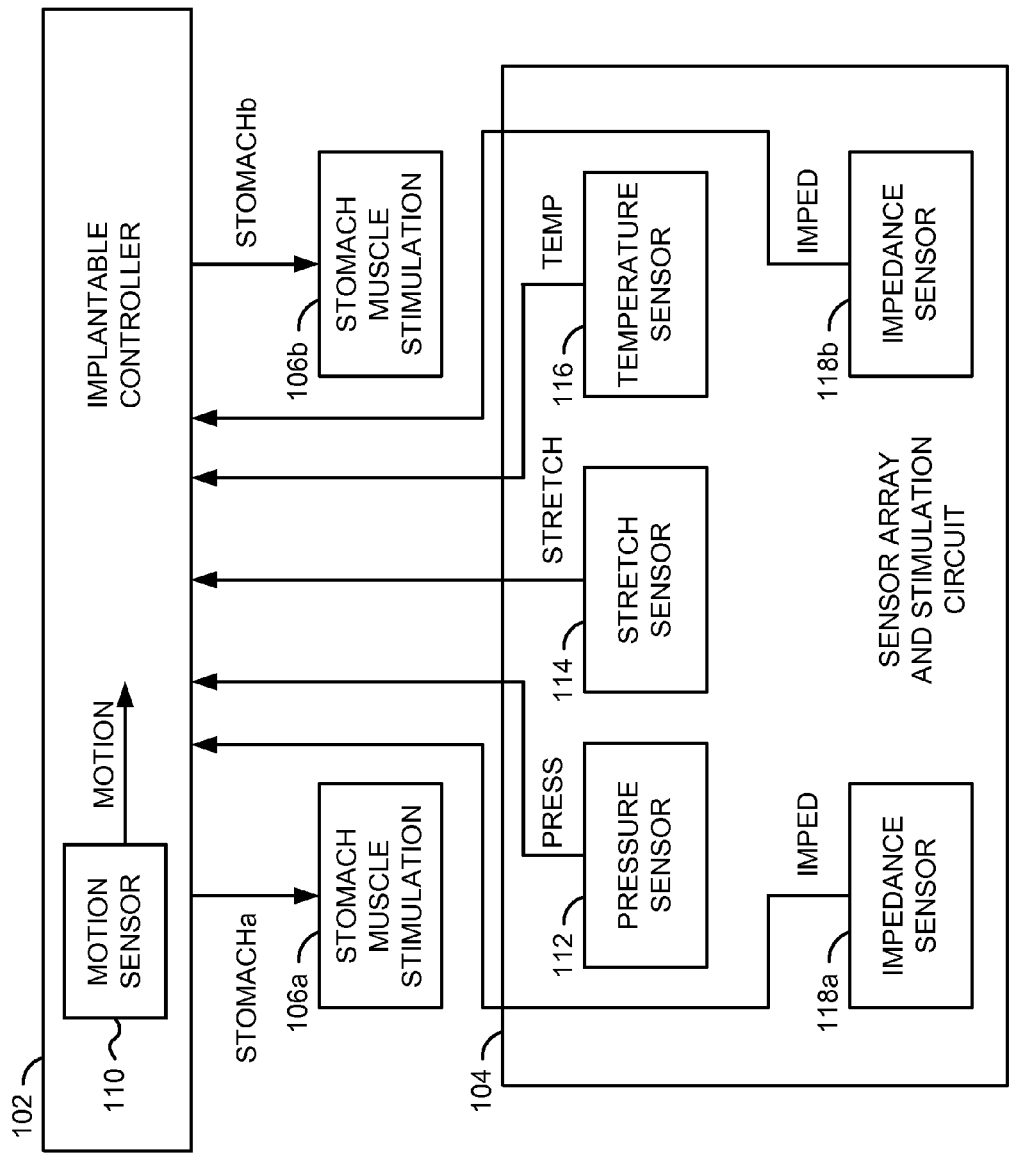
FIG. 2 is a block diagram of example implementations of an implantable controller circuit and a sensor array circuit.

Referring to FIG. 2, a block diagram of example implementations of the circuits 102 and 104 is shown. The circuit 102 may include a circuit (or unit) 110. The circuit 104 generally comprises a circuit (or unit) 112, a circuit (or unit) 114, a circuit (or unit) 116 and multiple circuits (or units) 118a-118b. A signal (e.g., MOTION) may be generated by the circuit 110 and used internal to the circuit 102. The circuits 110-118b may be implemented in hardware, firmware and/or software.

Returning to FIG. 1, the circuit 102 may implement an implantable controller unit suitable to be placed inside the patient. The circuit 102 is generally operational to process the data received in signals generated by the circuits 104 and 110 and information received through the signal RF to control stimulation of the stomach 20 and a vagus nerve 22 (e.g., the left vagus nerve). The circuit 102 may generate customized data by processing manual input data received from the patient and compare data using a set of rules. The manual input data and compare data may be received by the circuit 102 in the signal RF. The rules (i) are generally reprogrammable via the signal RF and (ii) may govern generation of the nerve stimulation signals carried by the signals STOMACHa, STOMACHb and VAGUS. The rules generally define predetermined control characteristics that may be applicable and customized to the patient. Some to all of the data received by the signals MOTION, TEMP, PRESS, IMPED and/or STRETCH may also be relayed through the circuit 102 and transmitted outside the patient in the signal RF.

The circuit 104 may be implemented as a sensor array and stimulation circuit. The circuit 104 may be implanted inside the patient on a surface (e.g., an antero-superid surface) of the stomach 20. The circuit 104 generally includes a suite of sensors (e.g., the circuits 112-118b) that generates the signals TEMP, PRESS, IMPED and STRETCH by monitoring the physical characteristics of the stomach 20. The signal TEMP may be generated by the circuit 116 to convey a temperature of the stomach 20. A pressure exerted by the stomach 20 on a diaphragm 24 of the patient may be sensed by the circuit 112 and reported in the signal PRESS. An electrical impedance across the antero-superid surface may be measured from one end of the circuit 104 to an opposing end and reported in the signal IMPED by the circuits 118a and 118b. A stretching of the stomach 20 (e.g., caused by eating) may be measured by the circuit 114 and transferred to the circuit 102 in the signal STRETCH.

Each of the circuits 106a-106b may implement a muscle stimulation electrode attached to muscles along the outer surface of the stomach 20. The circuits 106a-106b are generally operational to cause contractions of the muscles in response to the signal MUSCLE. In some embodiments, the signal MUSCLE may be implemented as a single signal that activates all of the circuit 106a-106b. In other embodiments, the signal MUSCLE may implement several signals, up to a respective signal for each of the circuits 106a-106b.

The circuit 108 may implement a nerve stimulation electrode coupled to the vagus nerve 22. The circuit 108 may be operational to transfer an electrical waveform in the signal VAGUS to the vagus nerve 22. The electrical waveform may be configured in terms of the frequency, the amplitude, the pulse width and the timing to provide a satiated feeling in the patient.

The circuit 110 may be implemented as a motion sensor. The circuit 110 may be operational to sense accelerations of the patient along one or more axis (e.g., X, Y and Z) of motion. Each axis may be defined relative to a housing of the circuit 102. Each acceleration may be reported as a separate component in the signal MOTION. The circuit 110 is generally used to measure activity levels of the patient that include, but are not limited to, recording a number to steps taken by the patient. The physical motion of the patient may be converted into electrical signals. The signal MOTION may also be used to charge an internal battery of the circuit 102.

Figure 3:
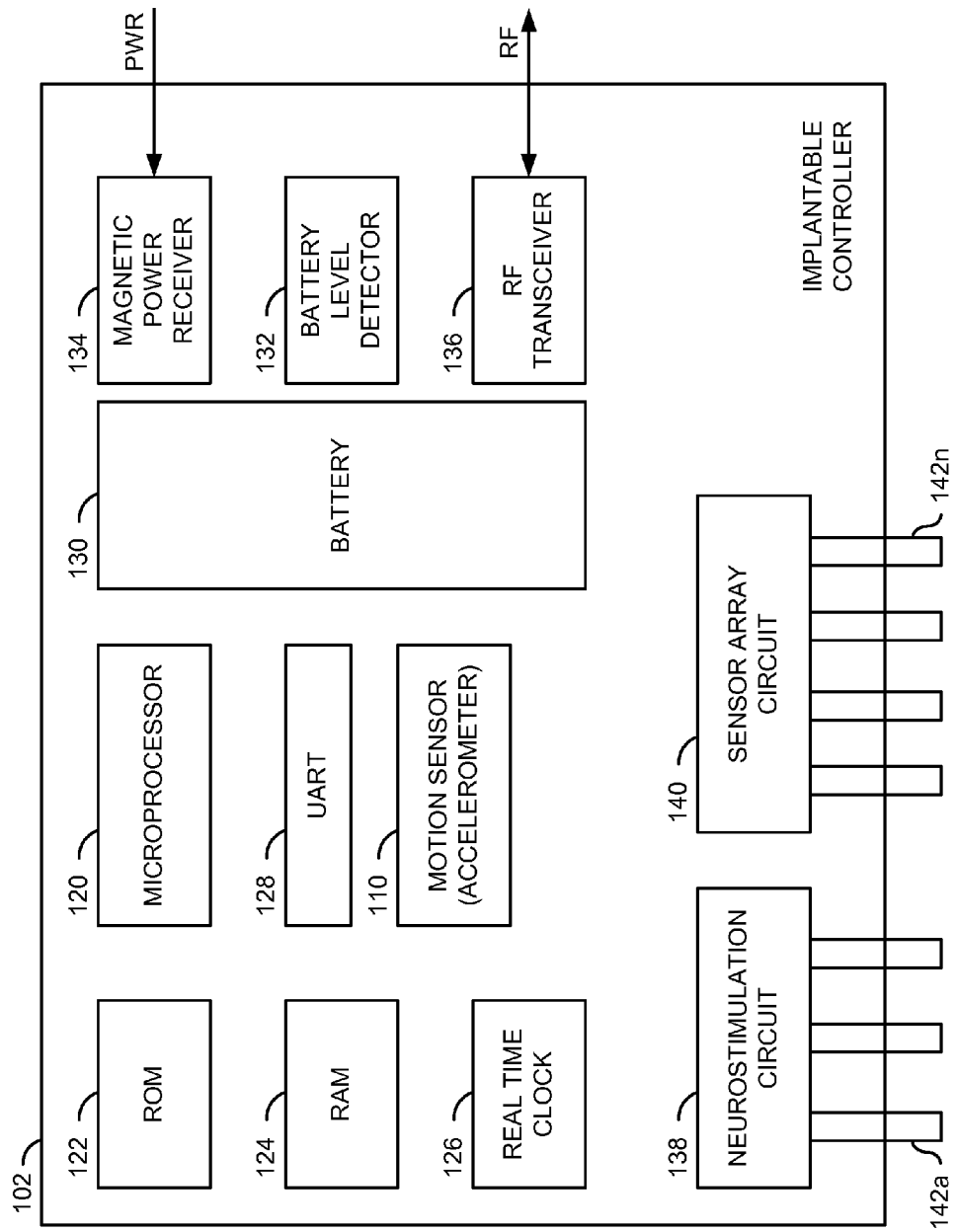
FIG. 3 is a detailed block diagram of an example implementation of the implantable controller circuit.

Referring to FIG. 3, a detailed block diagram of an example implementation of the circuit 102 is shown. The circuit 102 generally comprises the circuit 110, a circuit (or unit) 120, a circuit (or unit) 122, a circuit (or unit) 124, a circuit (or unit) 126, a circuit (or unit) 128, a circuit (or unit) 130, a circuit (or unit) 132, a circuit (or unit) 134, a circuit (or unit) 136, a circuit (or unit) 138 and a circuit (or unit) 140. Multiple pins 142a-142n may provide electrical connection between (i) the circuits 138 and 140 and (ii) the circuits 104, 106a-106b and 108. The signal RF may be transmitted and received by the circuit 136. A signal (e.g., PWR) may be received by the circuit 134. The circuits 120-140 may be implemented in hardware, firmware and/or software.

The circuit 120 may implement a microprocessor circuit. The circuit 120 is generally operational to control the signals STOMACHa-STOMACHb, VAGUS and RF by processing the data received by the circuit 102. The processing may include dynamic calibration of the stimulation signals STOMACHa-STOMACHb and VAGUS to increases the effectiveness of the therapy significantly. The circuit 120 may also be configured to execute a rules engine that governs the stimulation signals. Patient control of the rule-based stimulations may improve safety and reduce side effects by eliminating inadvertent therapy.

The circuit 122 may implement a Read Only Memory (ROM) circuit. The circuit 122 generally stores programming software executed by the circuit 120 to control the circuit 102. In some embodiments, the circuit 122 may implement an electronically erasable programmable ROM (EEPROM) such that the programming code may be updated remotely via the signal RF.

The circuit 124 generally implements a Random Access Memory (RAM) circuit. The circuit 124 may be used to buffer data received from the sensor and store intermediate data generated by the circuit 120.

The circuit 126 may be implemented as a real time clock circuit. The circuit 126 may be operational to generate clock signals representative of real time clock values (e.g., year, month, day, hour, minute and second). The clock signals may be used to trigger events such as a next round of neurostimulations, self-diagnostics operations, reporting the gathered data through the signal RF and the like.

The circuit 128 may be implemented as a Universal Asynchronous Receiver Transmitter (UART) circuit. The circuit 128 is generally operational to process transmit and receive protocols for communications via the signal RF. The circuit 128 may couple the circuit 120 to the circuit 136.

The circuit 130 may implement a battery that powers the circuit 102. In some embodiments, the circuit 130 may be a rechargeable battery.

The circuit 132 may be implemented as a battery level indicator circuit. The circuit 132 is generally operational to monitor the amount of power stored in the circuit 130. The power level available in the circuit 130 may be reported by the circuit 132 to the rules engine.

The circuit 134 may implement a power receiver circuit. The circuit 134 may be operational to receive power in the signal PWR. In some embodiments, the power may be in the form of a magnetic field. The signal PWR may be generated by a source external to the circuit 102. In some embodiments, the source may also be external to the patient. The power received by the circuit 134 is generally used to recharge the circuit 130 and provide electrical power to the rest of the circuitry within the circuit 102.

The circuit 136 may be implemented as a Radio-Frequency (RF) transceiver circuit. The circuit 136 generally provides for bidirectional communications between the circuit 102 and an external device. The circuit 136 may be coupled to the circuit 128 to (i) receive data that is being transmitted out of the circuit 102 and (ii) present received data to the circuit 128. The transmitted data may include, but is not limited to, the data collected by the various sensors, diagnostics and configuration data. The received data may include, but is not limited to, rule programs for the rules engine, compare data, calibration instructions and software program updates.

The circuit 138 may be implemented as a neurostimulation circuit. The circuit 138 is generally operational to generate the neurostimulation signals VAGUS and/or STOMACHa-STOMACHb. Generation of the neurostimulation signals may include varying the amplitude, frequency and pulse width of the signals.

The circuit 140 may be implemented as a sensor array circuit. The circuit 140 is generally operational to receive the sensor signals TEMP, PRESS, IMPED and STRETCH. The circuit 140 may also generate bias voltages, bias currents and/or reference frequencies for proper operation of the sensors in the circuit 104. The circuit 140 may also be operational to perform an analog to digital conversion of the sensor data.

Figure 4:
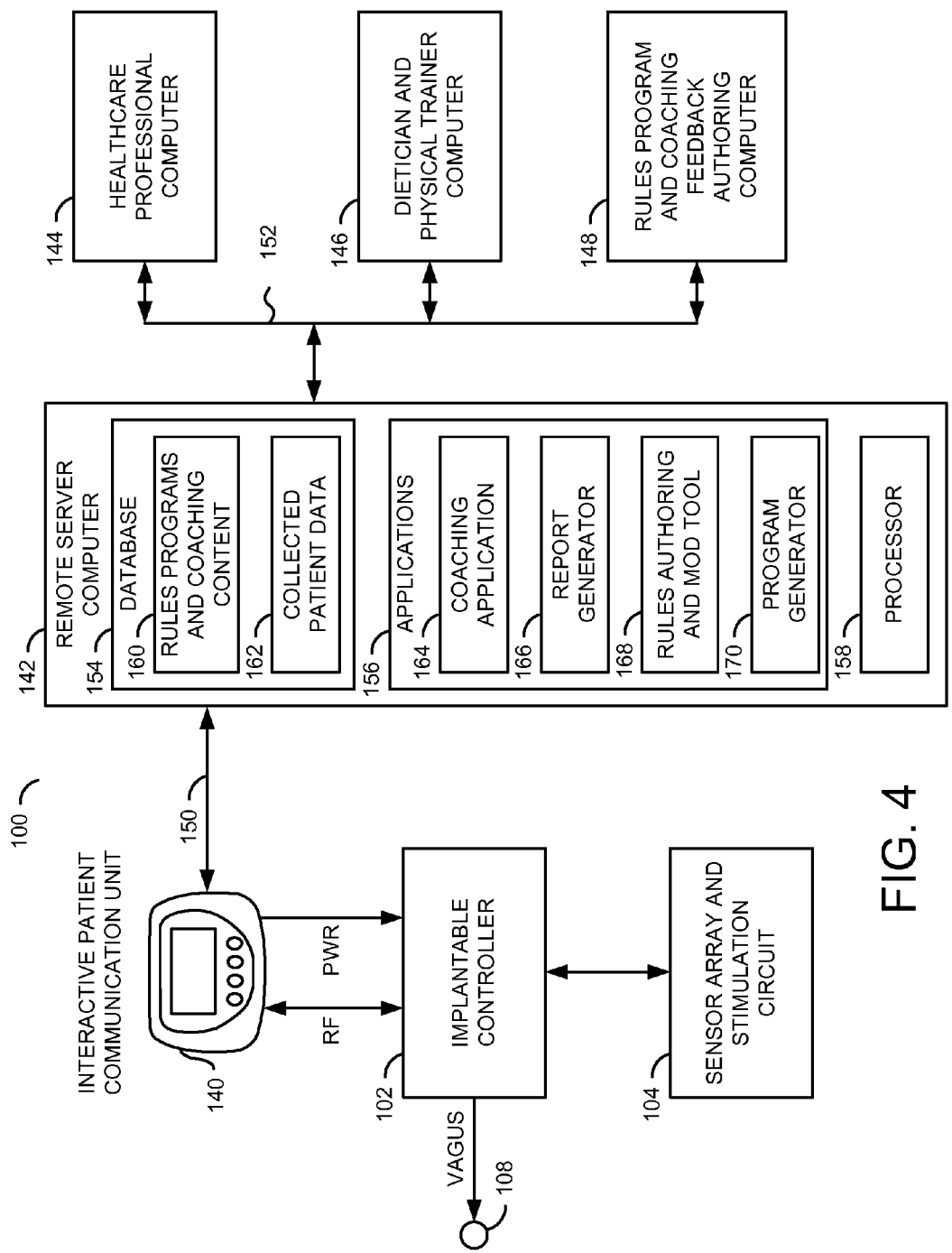
FIG. 4 is a block diagram of an example implementation of a system in accordance with a preferred embodiment of the present invention.

Referring to FIG. 4, a block diagram of an example implementation of the system 100 is shown in accordance with a preferred embodiment of the present invention. The system 100 generally includes the circuit 102, the circuit 104, the circuits 106a-106b (not shown), the circuit 108, a circuit (or unit) 140, a circuit (or unit) 142, a circuit (or unit) 144, a circuit (or unit) 146 and a circuit (or unit) 148. The circuit 140 may communicate with the circuit 102 via the signal RF. The signal PWR may be transmitted from the circuit 140 to the circuit 102. A communication channel 150 may be used for bidirectional communications between the circuit 140 and the circuit 142. A communication channel 152 may be used for bidirectional communications between the circuit 142 and the circuits 144, 146 and 148. In some embodiments, the communication channels 150 and 152 may be interconnected or may be the same (e.g., the Internet).

The circuit 140 may implement an interactive patient communication unit. The circuit 140 is generally operational to provide data transfers to and from the circuit 102 in the signal RF, provide power to the circuit 102 via the signal PWR and receive manual input data from the patient. The circuit 140 may transfer sensor data (e.g., motion, temperature, pressure, impedance and stretch) and diagnostics data from the circuit 102 to the circuit 142 over the channel 150. The rules programs, compare data, coaching content, software program updates and the like may be transferred from the circuit 142 to the circuit 102 through the circuit 140.

The circuit 140 may include a screen for displaying information to the user. The information may include, but is not limited to, the patient data collected from the sensors, coaching content received from the circuit 142, user adjustable parameters for customizing the neurostimulations, menus to receive user input data, instructions on how to use the circuits 140 and 102 and diagnostic results. The circuit 140 may also include multiple buttons, keys and/or switches configured for use by the patient. The buttons may be aligned with menus on the displays such that the patient may navigate through a menu structure, access data, enter rules parameters, make selections, response to questions (queries) and the like.

The circuit 142 may be implemented as a remote server computer. The circuit 142 is generally physically remote from the circuits 140, typically in another city or even another state. The circuit 142 may be operational to communicate with multiple circuits 140 concurrently over the communication channel 150. Data received from the circuits 140 may be stored in a database. From the database, the data may be remotely accessed by healthcare professionals, dieticians, physical trainers and technicians over the communication channel 152. The circuit 142 may be configured to generate compare data by comparing the physical data with profile data of the individual.

The circuit 144 may implement a healthcare professional computer. The circuit 144 is generally physically remote from the circuits 142. The circuit 144 is generally in bidirectional communication with the circuit 142 over the communication channel 152. The circuit 144 may enable a healthcare professional (e.g., doctor, physician, nurse, etc.) to access the patient information stored in the circuit 142 (e.g., stored in a database) and receive reports from the circuit 142.

The circuit 146 may implement a dietician and physical trainer computer. The circuit 146 is generally physically remote from the circuits 142. The circuit 146 is generally in bidirectional communication with the circuit 142 over the communication channel 152. The circuit 146 may enable a dietician and/or physical trainer to access the patient information stored in the circuit 142, adjust the rules applicable to the patients and adjust the coaching applications sent to the patients.

The circuit 148 may implement a rules and coaching feedback authoring computer. The circuit 148 may be physically remote from the circuits 142. The circuit 148 is generally in bidirectional communication with the circuit 142 over the communication channel 152. The circuit 148 may enable a user to access the patient information stored in the circuit 142, adjust the rules applicable to the patients and adjust the coaching applications sent to the patients.

The circuit 142 generally comprises a circuit (or unit) 154, a circuit (or unit) 156 and a circuit (or unit) 158. The circuit 154 may implement a database memory circuit. The database may be used to store rules and/or coaching content 160 and collected data 162 received from the patients. Other information may be stored in the circuit 154 to meet the criteria of a particular application. The circuit 156 generally comprises a collection of application (software) programs loaded in the circuit 142. The application programs may include one or more coaching application programs 164, one or more report generation programs 166, one or more rules authoring and modification tools 168 and one or more program generators 170. Other application programs may be included to meet the criteria of a particular application.

The circuit 158 may implement one or more processor circuits. The circuit 158 is generally operational to execute the application programs, operating system software, driver programs, communication utilities and the like to provide the functionality of the circuit 142. Other software applications, processor circuitry, networking circuitry, calendar/clock circuitry and the like may be implemented to meet the criteria of a particular application.

Figure 5:
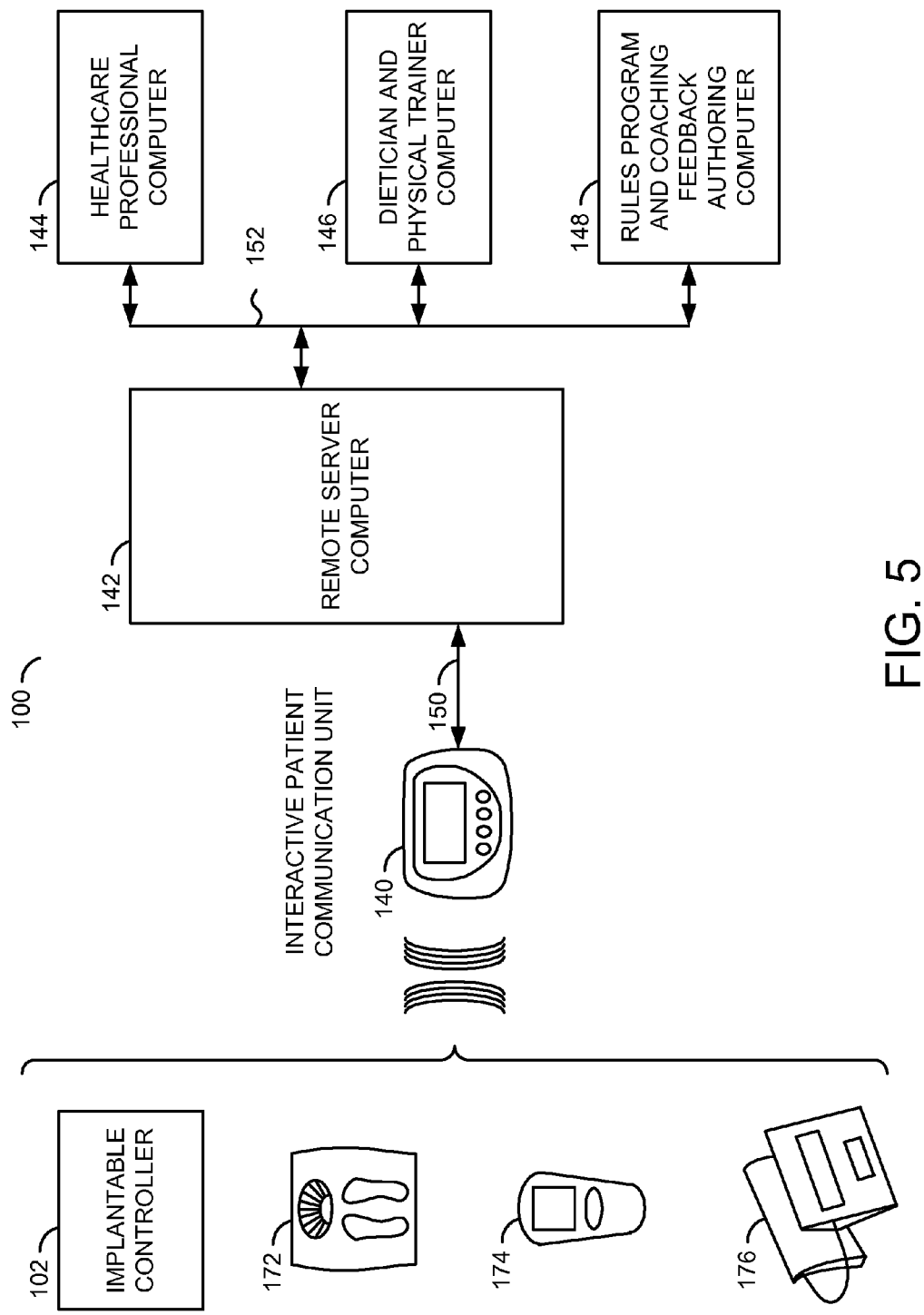
FIG. 5 is a block diagram of the system in combination with additional sensors.

Referring to FIG. 5, a block diagram of the system 100 in combination with additional sensors is shown. The additional sensors may be used to complement the sensors of the circuit 104 to provide additional information about the patient. The additional sensor as illustrated may include, but are not limited to, a scale 172, a blood glucose meter 174 and a blood pressure cuff 176. Other sensors may include a respiratory flow meter, an electrocardiogram and a pulse (heart) rate monitor. The specific type of sensors provided to each patient generally depends upon the health condition for which the patient is be monitored and/or treated. For example, diabetes patients may be provided with a blood glucose meter for measuring blood glucose concentrations, asthma patients may be provided with respiratory flow meters for measuring peak flow rates, obesity patients may be provided with weight scales and the like.

Each of the additional sensors may transfer the corresponding sensor data to the circuit 140 for collection and subsequent transmission to the circuit 142. Control and modifications to the sensor data collection may be provided using downloaded software programs generated by the program generator 170. The downloaded software programs may be generated in the circuit 142 and transferred to the circuit 140 over the communication channel 150. From the circuit 140, the downloaded software programs may be executed by a processor within the circuit 140 to gather the corresponding sensor data, buffer the sensor data internal to the circuit 140 and then transfer the sensor data over the communication channel 150 to the circuit 142. The circuit 142 may store the received sensor data in the circuit 154 for subsequent analysis by the application programs 156 and/or people at the computers 142-148. Additional information regarding the program generation application 170 and the resulting downloadable software programs may be found in co-pending U.S. application Ser. No. 10/233,296, which is hereby incorporated by reference in its entirety.

Communication between the circuit 140 and the additional sensors may be wired communications and/or wireless communications. Wired communications may be achieved using one or more standard communication interfaces of the circuit 140. For example, a Universal Serial Bus (USE) cable of the sensor 172 may be plugged into a USB port of the circuit 140 to transfer weight data of the patient. Wireless communications may use the same transceiver of the circuit 140 as is used by the circuit 136.

Figure 6:
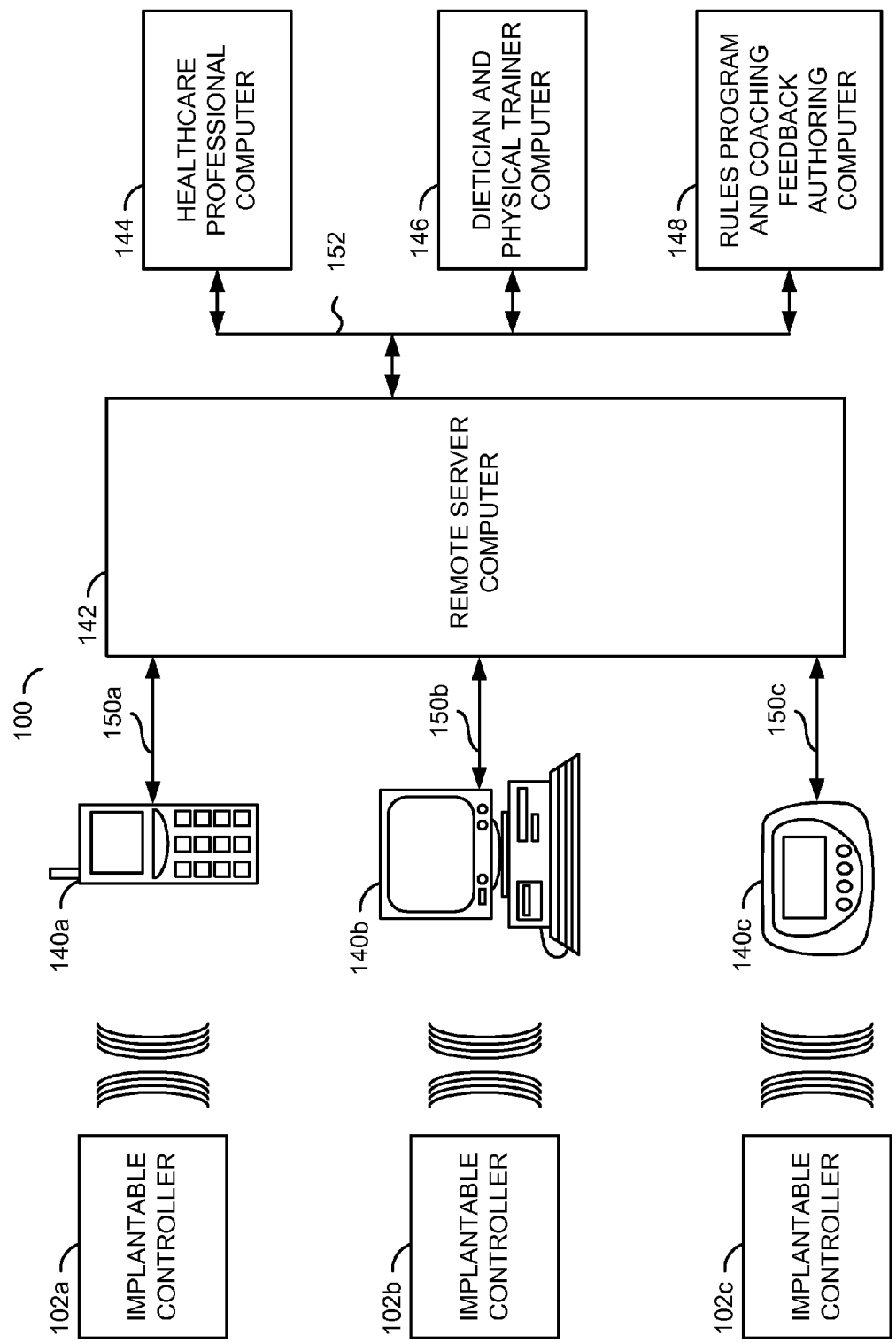
FIG. 6 is a block diagram of the system monitoring several patients.

Referring to FIG. 6, a block diagram of the system 100 monitoring several patients is shown. A single circuit 102 (e.g., circuits 102*a*-102*c*) may be implanted in each patient. Each patient may have an individual circuit 140 (e.g., circuits 140*a*-140*c*). Each of the circuits 140*a*-140*c* may have a corresponding communication channel 150 (e.g., communication channels 150*a*-150*c*) to the circuit 142.

The circuits 140*a*-140*c* may be functionally similar to each other, but may have different physical forms. For example, the circuit 140*a* may be implemented as a cellular telephone. The circuit 140*b* may be implemented as a personal computer. The circuit 140*c* may be implemented as a consumer telehealth appliance. Other embodiments of the circuit 140 may include, but are not limited to, laptop computers, notebook computers, netbook computers, personal digital assistants, Palm computers, and similar handheld portable processor-based devices.

Figure 7:
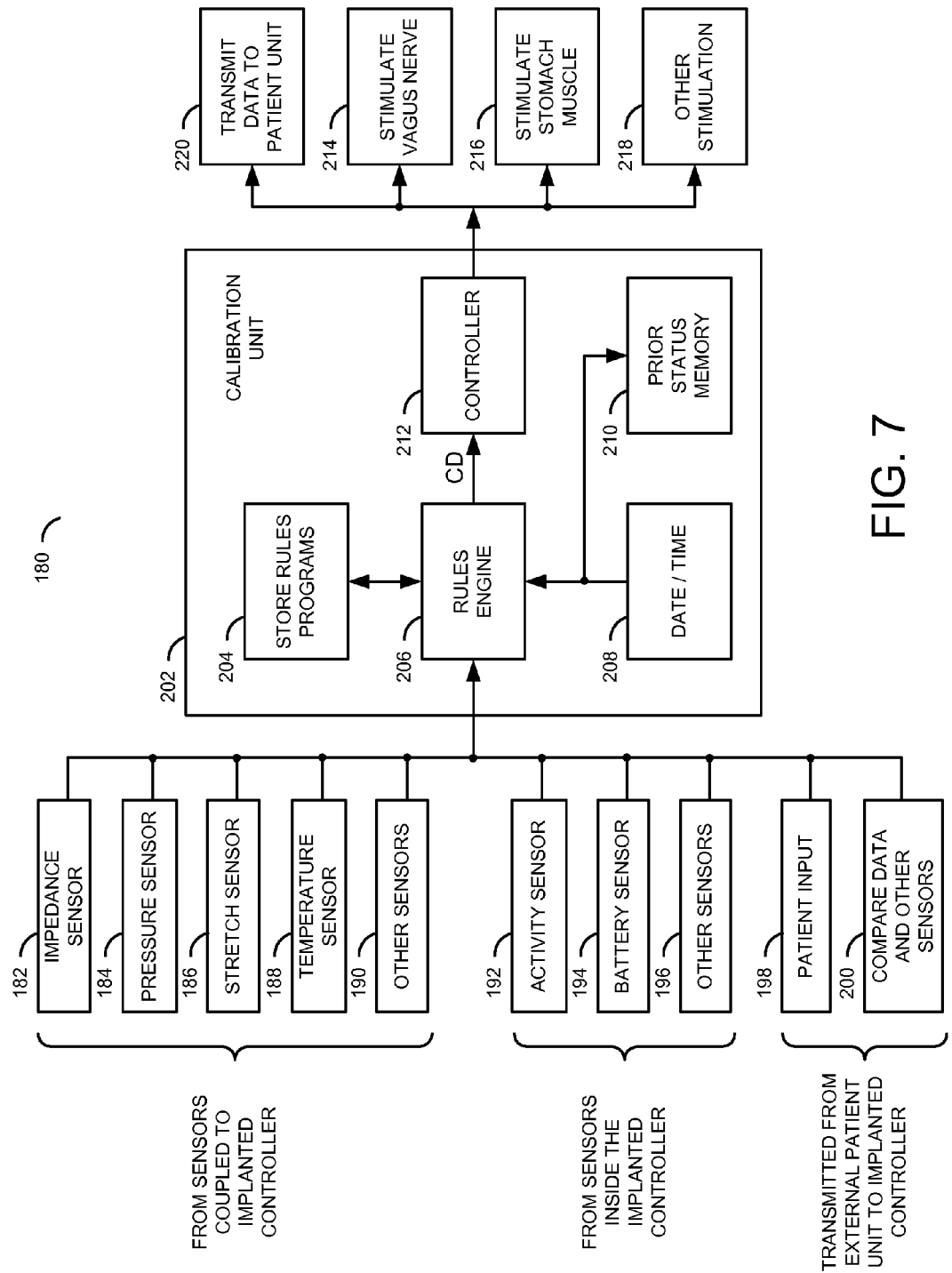
FIG. 7 is a function flow diagram of an example rules engine processing method.

Referring to FIG. 7, a function flow diagram of an example rules engine processing method 180 is shown. The method (or process) 180 generally comprises a step (or block) 182, a step (or block) 184, a step (or block) 186, a step (or block) 188, a step (or block) 190, a step (or block) 192, a step (or block) 194, a step (or block) 196, a step (or block) 198, a step (or block) 200, a step (or block) 202, a step (or block) 204, a step (or block) 206, a step (or block) 208, a step (or block) 210, a step (or block) 212, a step (or block) 214, a step (or block) 216, a step (or block) 218 and a step (or block) 220. The method 180 is generally implemented by the circuits 102 and 104. Each of the steps 182-220 may be implemented in hardware, firmware and/or software.

In the step 182, the circuits 118*a*-118*b* may sense an impedance and generate the signal IMPED. The circuit 112 may sense a pressure of the stomach 20 and generate the signal PRESS. The signal STRETCH may be generated by the circuit 114 in the step 186. In the step 188, the circuit 116 may sense a temperature and generate the signal TEMP. Other sensors (not shown) coupled to the circuit 102 may generate corresponding sensor signals in the step 190.

The circuit 110 may sense the physical activity of the patient in the step 192 and generate the signal MOTION accordingly. In the step 194, the circuit 132 may generate a signal indicating a status of the battery 130. Other sensors (not shown) internal to the circuit 102 may generate corresponding sensor signals in the step 196.

In the step 198, one or more manual inputs obtained by the circuit 140 may be received by the circuit 102 in the signal RF. Other sensor data obtained external to the patient (e.g., weight, blood pressure, etc.) and/or information transferred from the circuit 142 to the circuit 140 (e.g., compare data) may be received by the circuit 102 in the step 200.

The components of the circuit 102 may be configured as a calibration unit in the step 202. In the step 204, one or more rules programs may be read from the circuits 122 and/or 124 to the circuit 120. The circuit 120 may execute the rules programs in the step 206 to achieve the functionality of a rules engine. The rules engine may generate customized data in a signal (e.g., CD) during the step 206. The customized data may be based on the sensor data, the manual input data and the compare data received by the circuit 102, the date and time received from the circuit 126 in the step 208 and prior status information received from the circuits 122 and/or 124 in the step 210. The customization data is generally transferred to the circuit 138 where neurostimulation control is implemented in the step 212. The neurostimulation generally includes generating the signal VAGUS to stimulate the vagus nerve 22 in the step 214. The signals STOMACHa-STOMACHb may also be generated by the circuit 138 to stimulate the stomach muscles in the step 216. Other stimulation signals (not shown) may be created by the circuit 102 to perform other stimulations inside the patient in the step 218. The physical data of the patient collected by the sensors may be transmitted from the circuit 136 to the circuit 140 in the step 220.

Figure 8:
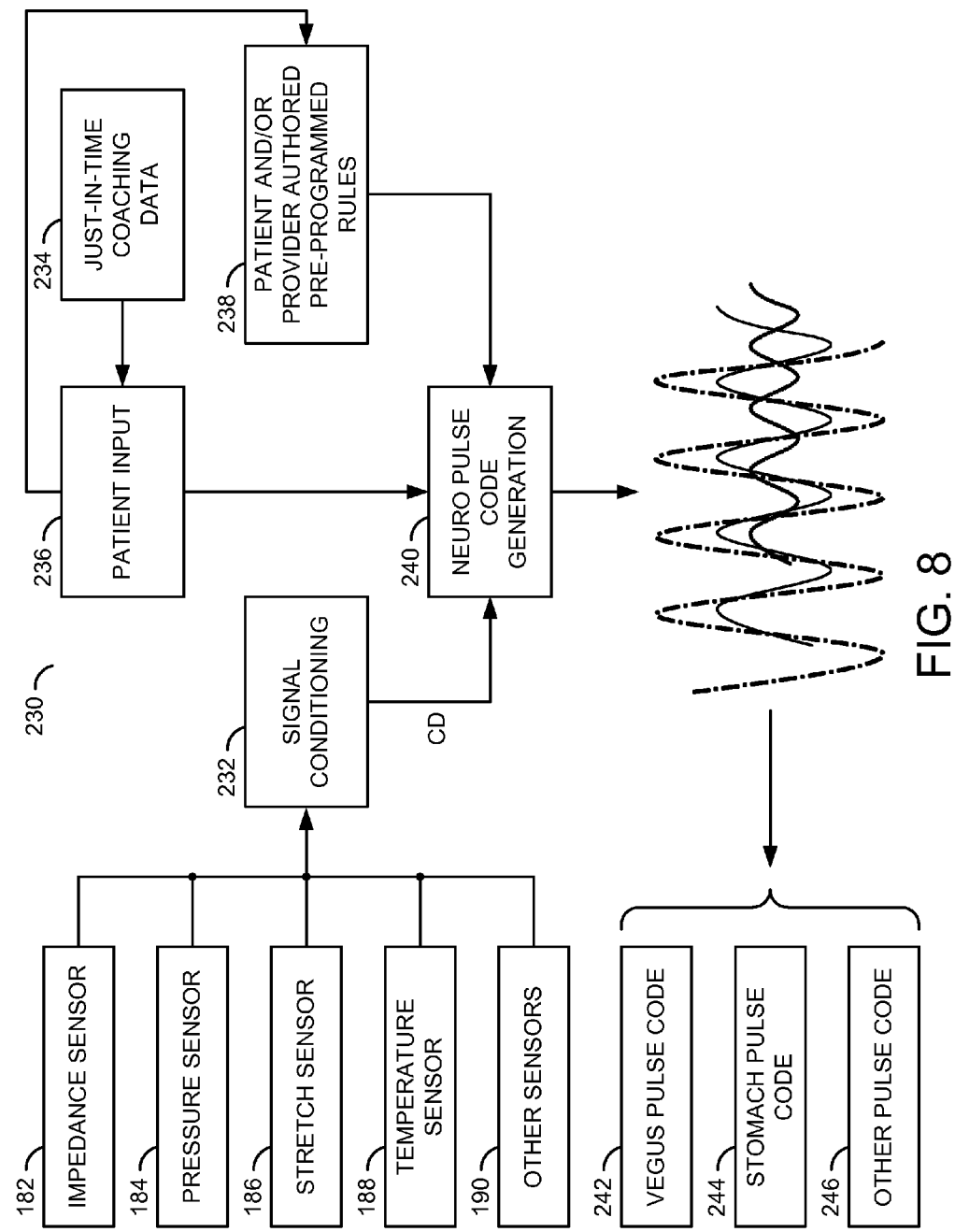
FIG. 8 is a functional flow diagram of an example neurostimulation method.

Referring to FIG. 8, a functional flow diagram of an example neurostimulation method 230 is shown. The method (or process) 230 generally comprises the step 182, the step 184, the step 186, the step 188, the step 190, a step (or block) 232, a step (or block) 234, a step (or block) 236, a step (or block) 238, a step (or block) 240, a step (or block) 242, a step (or block) 244 and a step (or block) 246. The method 230 may be implemented by the system 100.

In the steps 182-190, the sensor data may be generated and presented to the circuit 102. The sensor data may undergo signal conditioning by the circuit 102 in the step 232. In the step 234, just-in-time coaching data 160 may be presented from the circuit 142 to the circuit 140 and presented to the individual patient. The patient may use the coaching data and/or personal knowledge to enter manual inputs into the circuit 140 in the step 236. The manual inputs corresponding to the rules programs may be transferred back to the circuit 142 over the communication channel 150. The manual inputs directly associated with the neurostimulation may be transferred to the circuit 102 via the signal RF.

In the step 238, the manual inputs and/or healthcare provider information received from the circuits 144, 146 and/or 148 may be used by the circuit 142 to author and/or update one or more of the rules programs corresponding to the patient in the step 238. The new and/or updated rules programs may be transferred from the circuit 142 to the circuit 140 over the communication channel 150. The circuit 140 may transmit the rules programs to the circuit 102 in the signal RF. In the step 240, the circuits 120 and 138 may generate the neuro pulse codes 242 for the signal VAGUS, the pulse codes 244 for the signals STOMACHa-STOMACHb and/or other pulse codes 246 for internal neurostimulation of the patient.

Figure 9:
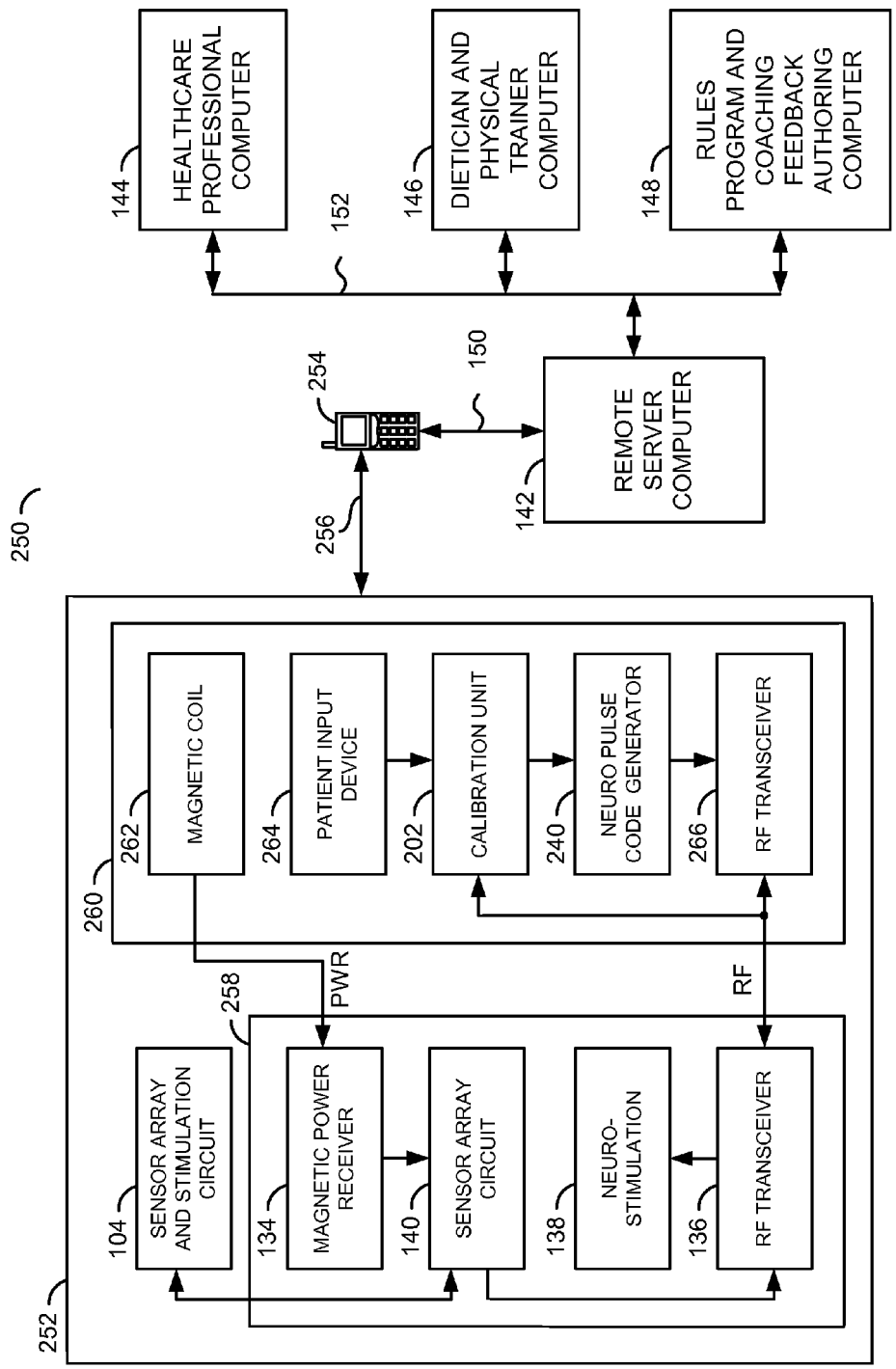
FIG. 9 is a block diagram of an example implementation of another system embodiment.

Referring to FIG. 9, a block diagram of an example implementation of a system 250 is shown. The system 250 may be a variation of the system 100. The system (or apparatus) 250 generally comprises the circuit 142, the circuit 144, the circuit 146, the circuit 148, the communication channel 150, the communication channel 152, a circuit (or unit) 252, a circuit (or unit) 254 and a communication channel 256. The communication channel 150 may provide bidirectional communication between the circuit 142 and the circuit 254. The communication channel 256 generally provides bidirectional communications between the circuit 252 and the circuit 254. The circuits 252-254 may be implemented in hardware, firmware and/or software.

The circuit 252 may implement a controller circuit. The circuit 252 is generally operational to process the data received from the sensors and information received through the communication channel 256 to control stimulation of the stomach muscles and the vagus nerve 22. The circuit 252 may generate customized data by processing manual inputs of the patient and compare data using the set of rules. The rules (i) are generally reprogrammable via the signal RF and (ii) may govern generation of the nerve stimulation signals carried by the signals STOMACHa, STOMACHb and VAGUS. The rules generally define predetermined control characteristics that may be applicable and customized to the patient. Some to all of the data received from the sensors may also be transferred to the circuit 142 over the communication channels 150 and 256.

The circuit 254 may be implemented as a wireless device. In some embodiments, the circuit 254 may be a cellular telephone, a personal computer, a wireless router, a consumer telehealth appliance, a laptop computer, a notebook computer, a netbook computer, a personal digital assistant, a Palm computer, and similar hand-held portable processor-based devices. The circuit 254 is generally operational to provide a link between the circuit 252 and the circuit 142.

The communication channel 256 may implement a wireless communication channel. In some embodiments, the communication channel 256 may be implemented as a Bluetooth channel. (Bluetooth is a registered trademark of Bluetooth Special Interest Group, Inc., Kirkland, Wash.) In other embodiments, the communication channel 256 may be implemented as a wi-fi channel. Other communication channels may be implemented to meet the criteria of a particular application.

The circuit 252 generally comprise the circuit 104, the circuits 106a-106b (not shown), the circuit 108 (not shown), a circuit (or unit) 258 and a circuit (or unit) 260. The circuit 260 may be coupled to the communication channel 256 for bidirectional communications with the circuit 142 through the circuit 254. The signal RF may provide bidirectional communications between the circuit 260 and the circuit 258. The signal PWR may transfer magnetic power from the circuit 260 to the circuit 258.

The circuit 258 may implement a version of the circuit 102. The circuit 258 may be implantable in the patient. In some embodiments, the circuit 258 may comprise the circuit 110 (not shown), the circuit 128 (not shown), the circuit 134, the circuit 136, the circuit 138 and the circuit 140. The circuit 128 may be coupled to the circuit 138 to transfer the sensor data through the circuit 136 to the circuit 260. The circuit 140 may be coupled to the circuit 128 to receive the neuro pulse codes through the circuit 136 from the circuit 260. The circuit 258 may power up and operate while receiving power via the signal PWR. The signal PWR may be generated upon activation of the circuit 260 by the user (e.g., patient).

The circuit 260 may implement a wearable version of the circuit 140. The circuit 260 generally comprises the calibration unit 202, the neuro pulse code generator 240, a circuit (or unit) 262, a circuit (or unit) 264 and a circuit (or unit) 266. The circuit 262 may generate the signal PWR. The circuit 266 may communicate with the circuit 136 using the signal RF. The circuits 262-266 may be implemented in hardware, firmware and/or software.

The circuit 262 may implement a magnetic coil and associated circuitry. The circuit 262 is generally operational to generate the signal PWR to drive the circuit 258 (or the circuit 102 in the system 100). The circuit 262 may provide continuous power to the circuit 258 while the circuit 260 is active. In some embodiments, the circuit 262 may provide power on an as-requested basis to recharge the battery of the circuit 102, as determined by the circuit 132.

The circuit 264 may implement a user interface circuit. The circuit 264 is generally operational to obtain the manual input data from the patient and present coaching data and other information to the patient. In some embodiments, the manual input data may be obtained from keys, switches and/or buttons. In other embodiments, the manual input data may be obtained via menus, cursors and/or voice recognition.

The circuit 266 may implement a RF transceiver circuit. The circuit 266 is generally operational to communicate with the circuit 136 using the signal RF. The circuit 266 may transfer the patient sensor data from the circuit 104 to the circuit 202 for use in customization of the neuro pulse codes. The circuit 266 may also send the neuro pulse code information from the circuit 240 to the circuit 138 for stimulating the patient.

Processing of the sensor physical data, manual input data and the compare data may be performed by one or more processors (not shown) in the circuit 260 executing the calibration unit 202 and the neuro pulse code generator 240. The circuit 260 generally stores the rules to translate the sensor data and manual input data locally and transfers a copy of the manual input data and the sensor data to the circuit 142 using the circuit 254 and the communication channels 256 and 150.

The manual input data received from the user may be used in a feedback loop of the neurostimulation. For example, manual data entered into the circuit 264 may be passed to the calibration unit 202. Concurrently, sensor data collected by the circuit 104 may be transferred to the circuit 136, transmitted to the circuit 266 and sent to the calibration unit 202. The calibration unit 202 may process the manual input data and the sensor data per the rules to generate customized data for stimulating the patient. The customized data may be presented to the circuit 240 to control generation of one or more neuro pulse codes. The circuit 240 may present the neuro pulse codes to the circuit 266. The circuit 266 may transmit the neuro pulse code data to the circuit 136. The circuit 136 may present the neuro pulse code data to the circuit 138 where the neuro pulse codes are converted into the electrical signals VAGUS and/or STOMACHa-STOMACHb. The sensor data and the manual input data may be transferred from the circuit 260 to the circuit 254 over the communication channel 256. The circuit 264 may transfer the manual input data from the circuit 254 over the communication channel 150 to the circuit 142 for storage in the database 154 as the collected data 162.

Remote monitoring of the collected data 162 may be performed by one or more healthcare professionals using one or more circuits 144 and one or more dieticians and/or physical trainers using one or more circuits 146. The monitoring may include viewing the raw collected data 162 and/or reading one or more reports created by the report generator 166. The healthcare professions, dieticians and/or physical trainers may assist in the treatment of the patient by adding to, deleting from and/or modifying the rules using the circuit 168. Other providers may also adjust the rules from the circuit 148. The adjusted rules may be stored in the database 154. The program generator 170 may compile the rules into programs once the adjustments have been completed and forward the rules programs to the circuit 260. Additions, deletions and/or modification may also be made to the coaching content 160. The coaching applications 164 may transfer the adjusted coaching content to the circuit 260 for display to the patient.

Using the just-in-time coaching and the rule programs the patient may initiate the neurostimulation activity that results in generation of the neuro pulse codes containing the frequency/amplitude values of the neurostimulation waveforms (signals). The patient involvement supported by the just-in-time coaching data generally results in long term reduction of neurostimulation activities. Reductions in the neurostimulation activities may decrease the likelihood of potential side effects and increased safety of the patient. The reductions in the neurostimulation activities may also decrease the power consumption of the circuits 102, 104 and/or 252 that generally results in reduction in size of the implantable devices and increased patient comfort, both during implant and device operation.

In addition to obesity management treatments, the systems 100 and/or 250 may be useful in other addictive disorders and/or mental disorders. For example, the systems 100 and/or 250 may be used to treat smoking and/or drug abuse situations. Application of the neurostimulation may also aid in the restoration of normal breathing, reduce or eliminate pain, restore sexual functions, help regulate bladder and bowel functions and aid the patient in controlling walking and/or arm movements. Other treatments dealing with neurostimulation and/or muscle stimulations may be implemented to meet the criteria of a particular application.

The functions performed by the diagrams of FIGS. 1-9 may be implemented using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), video digital signal processor (VDSP) and/or similar computational machines, programmed according to the teachings of the present specification, as will be apparent to those skilled in the relevant art(s). Appropriate software, firmware, coding, routines, instructions, opcodes, microcode, and/or program modules may readily be prepared by skilled programmers based on the teachings of the present disclosure, as will also be apparent to those skilled in the relevant art(s). The software is generally executed from a medium or several media by one or more of the processors of the machine implementation.

The present invention may also be implemented by the preparation of ASICs (application specific integrated circuits), Platform ASICs, FPGAs (field programmable gate arrays), PLDs (programmable logic devices), CPLDs (complex programmable logic device), sea-of-gates, RFICs (radio frequency integrated circuits), ASSPs (application specific standard products) or by interconnecting an appropriate network of conventional component circuits, as is described herein, modifications of which will be readily apparent to those skilled in the art(s).

The present invention thus may also include a computer product which may be a storage medium or media and/or a transmission medium or media including instructions which may be used to program a machine to perform one or more processes or methods in accordance with the present invention. Execution of instructions contained in the computer product by the machine, along with operations of surrounding circuitry, may transform input data into one or more files on the storage medium and/or one or more output signals representative of a physical object or substance, such as an audio and/or visual depiction. The storage medium may include, but is not limited to, any type of disk including floppy disk, hard drive, magnetic disk, optical disk, CD-ROM, DVD and magneto-optical disks and circuits such as ROMs (read-only memories), RAMS (random access memories), EPROMs (electronically programmable ROMs), EEPROMs (electronically erasable ROMs), UVPROM (ultra-violet erasable ROMs), Flash memory, magnetic cards, optical cards, and/or any type of media suitable for storing electronic instructions.

The elements of the invention may form part or all of one or more devices, units, components, systems, machines and/or apparatuses. The devices may include, but are not limited to, servers, workstations, storage array controllers, storage systems, personal computers, laptop computers, notebook computers, palm computers, personal digital assistants, portable electronic devices, battery powered devices, set-top boxes, encoders, decoders, transcoders, compressors, decompressors, pre-processors, post-processors, transmitters, receivers, transceivers, cipher circuits, cellular telephones, digital cameras, positioning and/or navigation systems, medical equipment, heads-up displays, wireless devices, audio recording, storage and/or playback devices, video recording, storage and/or playback devices, game platforms, peripherals and/or multi-chip modules. Those skilled in the relevant art(s) would understand that the elements of the invention may be implemented in other types of devices to meet the criteria of a particular application.

While the invention has been particularly shown and described with reference to the preferred embodiments thereof, it will be understood by those skilled in the art that various changes in form and details may be made without departing from the scope of the invention.

The invention claimed is:

1. A method for personalized patient controlled neurostimulation, comprising the steps of:
   (A) obtaining (i) physical data of an individual and (ii) one or more manual inputs from said individual;

(B) transmitting said physical data via a communication channel to a processor circuit external to said individual;
(C) generating compare data in said processor circuit by comparing said physical data with profile data of said individual;
(D) transmitting said compare data from said processor circuit via said communication channel to a controller;
(E) generating customized data in said controller by processing said one or more manual inputs and said compared data using a set of rules, wherein said rules are (i) reprogrammable and (ii) govern generation of a nerve stimulation signal having predetermined control characteristics applicable to said individual;
(F) controlling said neurostimulation of said individual with said nerve stimulation signal based on said customized data and;
(G) presenting feedback information to said individual of one or more health-related conditions of said individual, wherein said feedback information advises said individual to alter at least one of (i) a physical characteristic of said individual and (ii) a behavioral characteristic of said individual.

2. The method according to claim 1, wherein said physical data comprises at least one of (i) eating data of said individual and (ii) exercising data of said individual.

3. The method according to claim 1, wherein said neurostimulation treats at least one of (i) an addictive disorder of said individual, (ii) a mental retardation of said individual and (iii) a pain of said individual.

4. The method according to claim 1, wherein said neurostimulation controls a weight of said individual.

5. The method according to claim 1, wherein said nerve stimulation signal is applied to a vagus nerve of said individual.

6. The method according to claim 1, wherein said obtaining of said one or more manual inputs from said individual occurs using an interactive communication unit.

7. The method according to claim 6, wherein said interactive communication unit comprises at least one of (i) a cellular phone, (ii) a computer and (iii) a personal digital assistant.

* * * * *